United States Patent
Hintsche et al.

[11] Patent Number: 5,830,343
[45] Date of Patent: Nov. 3, 1998

[54] ELECTROCHEMICAL ANALYSIS PROCESS

[75] Inventors: Rainer Hintsche, Berlin; Manfred Paeschke, Basdorf; Albrecht Uhlig, Berlin, all of Germany

[73] Assignee: Fraunhofer-Gesellschaft zur Foerderung der angewandten Forschung e.V., Munich, Germany

[21] Appl. No.: 613,621

[22] Filed: Mar. 11, 1996

Related U.S. Application Data

[63] Continuation-in-part of PCT/DE95/00847, Jun. 28, 1995.

[30] Foreign Application Priority Data

Jul. 11, 1994 [DE] Germany ............... 44 24 355.3

[51] Int. Cl.⁶ .................................................. G01N 27/26
[52] U.S. Cl. .................. 205/775; 204/413; 204/434; 205/789.5
[58] Field of Search .................. 204/413, 434, 204/415; 205/775, 789, 789.5

[56] References Cited

U.S. PATENT DOCUMENTS

| | | | |
|---|---|---|---|
| Re. 32,920 | 5/1989 | Matson et al. ............... | 204/412 |
| 3,904,487 | 9/1975 | Lieberman et al. . | |
| 5,120,421 | 6/1992 | Glass et al. . | |
| 5,217,112 | 6/1993 | Almon . | |
| 5,284,567 | 2/1994 | Matson . | |
| 5,290,420 | 3/1994 | Matson . | |
| 5,298,146 | 3/1994 | Braden et al. ............... | 204/415 |
| 5,415,760 | 5/1995 | Hitomi et al. ............... | 204/415 |

FOREIGN PATENT DOCUMENTS

| | | |
|---|---|---|
| 25 42 863 | 3/1977 | Germany . |
| 27 11 989 | 4/1980 | Germany . |
| 41 36 779 | 5/1993 | Germany . |
| 2 284 892 | 6/1995 | United Kingdom . |
| WO 91/08474 | 6/1991 | WIPO . |

OTHER PUBLICATIONS

*Review of Scientific Instruments*, 60 (1989) Oct., No. 10, New York, pp. 3323–3328 entitled "Multiple Electrode Potentiostat" by M.S. Harrington, et al.

Analytical Chemistry, 64 (1992) Jan. 15, No. 2, Washington, D.C., pp. 151–155 entitled "Mercury–Coated Carbon–Foam Composite Electrodes for Stripping Analysis of Trace Metals" by J. Wang et al.

*Primary Examiner*—T. Tung
*Attorney, Agent, or Firm*—Evenson, McKeown, Edwards & Lenahan PLLC

[57] ABSTRACT

A process is provided for the electrochemical analysis of compounds of solutions, such as can, e.g., be used in chemical analysis or for control measurements in industrial and environmental sectors. Identification or detection of individual substances takes place by the deposition thereof on electrodes and subsequent detection of the deposited substances. In the process, use is made of a plurality of electrodes. The substances to be identified from the solution are so simultaneously deposited on the electrodes that each electrode is coated with a different substance or substance mixture. Then, the deposited substances are simultaneously identified on the individual electrodes. Thus, the measuring time is significantly shortened and the risk of faulty measurements due to interactions between the substances to be identified on the electrodes is significantly reduced.

8 Claims, 1 Drawing Sheet

ELECTROCHEMICAL ANALYSIS PROCESS

CROSS-REFERENCE TO RELATED APPLICATIONS

This application is a continuation-in-part of PCT Application No. PCT/DE95/00847 filed on Jun. 28, 1995.

BACKGROUND AND SUMMARY OF THE INVENTION

The invention relates to a process for the electrochemical analysis of compounds of solutions, such as are e.g. usable in analytical chemistry or for control measurements in the industrial and environmental sectors.

The identification of individual substances, such as e.g. heavy metals, takes place by means of the enrichment or concentration thereof on electrodes by deposition and subsequent detection of the deposited substances. Deposition can e.g. take place by reduction on amalgamed noble metal electrodes made from mercury, other metals or carbon and detection by subsequent oxidation of the deposited substance.

W. R. Mattson et al., Anal. Chem. 3.7., p 1594, 1965 discloses a heavy metal identification process operating according to this principle, where use is made of a mercury film electrode. Numerous applications based on this publication are described in the literature under the term "stripping analysis". Thus, e.g. Florence T. M., J. Electroanal. Chem., 1970, 27, p 237 describes the deposition of a thin mercury film on glass-carbon for stripping analysis. Y. Shao et al., 44th ISE Meeting Abstracts, p 560, 1993 also describes the possibility of structuring individual electrodes to conductively interconnected microelectrodes.

However, in the known processes in each case only one (working) electrode is used, on which several substances are deposited by the application of a correspondingly high potential. The identification of the deposited substances takes place by scanning a wide potential range within which the individual substances are successively reoxidized and consequently identified. Through the deposition of numerous substances on an electrode, interactions can occur between these substances (e.g. intermetallic interactions, such as alloy formation), which falsify the later measured result. In addition, the measuring time is significantly increased with a growing number of substances to be identified.

Therefore, the problem of the present invention is to develop a process for electrochemical analysis in which the measuring time is significantly reduced and the risk of faulty measurements due to interactions between the substances to be detected on the electrodes is significantly decreased.

The solution of this problem according to the invention provides a process for electrochemical analysis, in which a reference electrode and several electrodes, which can be supplied with electrical potentials independently of one another, are brought into contact with a solution to be analyzed. Substances from the solution are simultaneously deposited on the electrodes in such a way that each electrode is coated with a different substance or a different substance mixture, and the deposited substances are subsequently and approximately simultaneously identified on the individual electrodes.

The process according to the invention is based on the use of a multiple array of electrodes, which are present as volume material or in thin film form. The detection or identification of individual substances is based on their enrichment or concentration on electrodes by deposition, e.g. by reduction on metals or carbons, as well as their subsequent detection, e.g. by oxidation. This process permits the determination of all chemical substances, which are reversibly deposited at one electrochemical potential and can be brought into solution again at another electrochemical potential.

According to the invention, a plurality of electrodes, e.g. in array form, are brought into contact with the solution to be analyzed. The substances to be identified are simultaneously deposited on the individual electrodes, each electrode being coated with a different substance or a different substance mixture. This can e.g. be brought about in that the different electrodes are at the same time subject to different potentials. The potentials on the individual electrodes are chosen in such a way that on each electrode the substance to be identified therewith is deposited. The identification of the deposited substances, e.g., takes place by a time-simultaneous scanning of the different electrodes in different potential windows or ranges. These potential windows are also chosen in such a way that with them is possible the identification of the particular substance deposited on the electrode.

With the selective coating of individual electrodes with a mercury film and a precious metal electrode left free (e.g. a gold electrode), it is possible to identify mercury, as well as other heavy metals. As a result of the simultaneous application of different potentials to the individual electrodes, metals or other molecules are selectively deposited on the individual electrodes. Thus, in an advantageous manner, interference with the analysis process by intermetallic interactions of simultaneously deposited species on the electrodes is prevented. In each case, the identification of one substance on, in each case, one electrode is made possible by the scanning of different potential ranges on the electrodes. This potential range scanning process takes place approximately simultaneously, so that as a result the analysis time is significantly reduced. Therefore, in an advantageous manner, the process permits the rapid, parallel, i.e., simultaneous, detection of several substances.

In an embodiment according to the present invention, a different potential is simultaneously applied to the individual electrodes. Through the choice of the electrode potential, the deposition of specific substances (e.g. metals) on an electrode can be prevented, but encouraged on another electrode.

According to a preferred embodiment, for the identification of the deposited substances, each electrode is scanned approximately simultaneously in a specific potential range. This can, e.g., take place by means of a potential ramp, on which are superimposed potential pulses or alternating voltages. Through the choice of the potential ranges of the potential ramps, which are simultaneously scanned on the individual electrodes, in each case one metal or other substance is reoxidized on each electrode, so that in each case one substance, e.g. a metal, is in each case detected on an electrode.

In a further preferred embodiment according to the invention, use is made of electrodes which either have a volume-like (e.g. spherical or cylindrical) form or are planar. The individual electrodes can in each case be formed from individual bunched (e.g. carbon fibers) or planar, grid-like microelectrodes. As a result of this structuring of the individual electrodes, the electrode reactions become independent of the mass transfer. The deposition of a homogeneous mercury film on the microelectrodes is also made possible.

The electrodes used in the process according to the invention can, e.g. be of metal, metal oxide or carbon.

According to a further preferred embodiment, in the process use is made of electrodes made from different materials (several electrode types). Thus, through the choice of the electrode material, it is possible to attain selectivity with respect to the material deposited on the electrode.

According to a still further preferred embodiment, a mercury film can be produced in a variable manner on one or several electrodes. Thus, it is possible to, as desired, enrich by amalgamation or film formation the substances or ions to be identified.

According to another embodiment, the individual electrodes can be arranged in a flow channel, e.g. in array form in a flow channel or flow duct. The flow channel permits the supply of the electrode array with different analytes and solutions.

For coating the individual electrodes with a mercury film or for the subsequent detachment thereof, the electrodes are brought into contact with a mercury-containing electrolyte in a further preferred embodiment.

According to yet another preferred embodiment, when using a flow channel, it is possible to employ two separate circuits, a first circuit with the mercury-containing electrolyte and a second with the solution to be analyzed. Therefore, the electrolyte to be measured can be moved past the electrode array, without it coming into contact with the electrolyte used for producing the mercury film.

The advantages of the process according to the invention are that several electrodes, e.g. in the form of an electrode array, can be used for the simultaneous detection of several substances (e.g. heavy metals). Thus, compared with the conventional stripping analysis process, a qualitative improvement and a shortening of the measuring time are obtained. It is also possible to prevent interference to the measurement process by the interaction of the enriched substances. This is achieved by the selective deposition of the different substances on different electrodes. The structuring of the individual electrodes as microelectrodes advantageously permits a convection-independent operation and, in particular, a homogeneous deposition of mercury films. The process also permits the use of mercury-coated and mercury-free metal electrodes, so that it is possible in parallel to detect mercury, as well as other heavy metals.

The invention is described in greater detail hereinafter relative to an embodiment and the attached drawing, which shows in exemplified form an embodiment of an electrode array for performing the process according to the invention.

BRIEF DESCRIPTION OF THE DRAWING

The FIG. 1A is a schematic diagram of an electrode array for performing the process according to the present invention.

DETAILED DESCRIPTION OF THE DRAWING

Figure 1A:
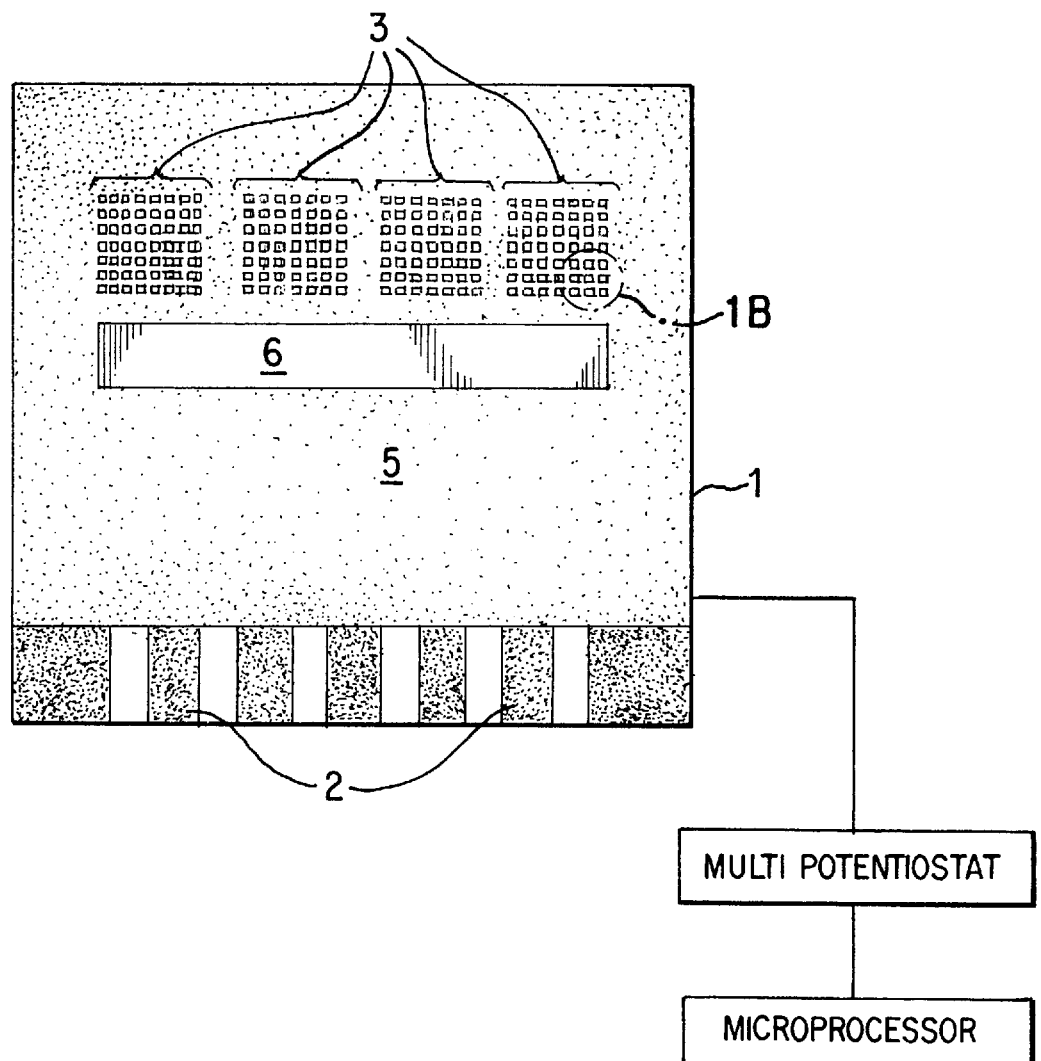
FIG. 1B is an enlarged detailed view of a portion of an electrode of FIG. 1A.
Figure 1B:
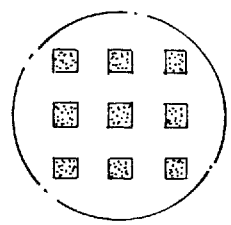

Referring to the figures, the electrode array is in the form of a planar multi-electrode array formed in silicon technology. Four electrodes 3, as well as a reference electrode 6, are arranged in an array-like manner on a silicon chip 1 having an oxidation coating 5. The individual electrodes 3, 6 are conductively connected to the associated contact faces 2. The individual electrodes 3 are once again microstructured. They consist of a plurality of individual, planar, grid-like microelectrodes 4.

The embodiment shows the use of the process according to the invention for the simultaneous determination of the metals bismuth, copper, lead and cadmium in a solution. Use is made of the structure shown in the drawing. The four individual electrodes 3 comprise in each case 32 platinum electrodes 4 with a surface area of 25 $\mu m^2$ each. The four electrodes 3 could also comprise a thousand (1000) platinum electrodes, each with a surface area of 25 $\mu m^2$. Each electrode 3 is used for the identification of one of the four metals to be detected. The silver chloride electrode 6 is used for fixing the reference potential.

Prior to the performance of the process, the silicon chip 1 is capped, i.e. protected against liquid influences on the chip leads or lines. The structure is then immersed in a solution with a mercury containing solution and connected to a multipotentiostat controlled by a microprocessor. The multipotentiostat brings the electrodes to an individual potential and can detect the resulting current. By means of a computer-assisted program, a mercury film is electrodeposited on all electrodes. Thereafter, the electrodes are rinsed with pure water. By means of a computer-assisted program, for the first electrode there is a deposition potential for the first electrode of –0.2 V for bismuth, for the second electrode a deposition potential of –0.4 V for copper and bismuth, for the third electrode –0.6 V for lead, copper and bismuth and for the fourth electrode –0.8 V for cadmium, lead, copper and bismuth. Alternatively, there is a deposition potential of –0.3 V for copper, for the second electrode a deposition potential of –0.5 V for lead and copper, for the third electrode –0.8 V for cadmium, lead and copper, and for the fourth electrode –1.1 V for zinc, cadmium, lead and copper. By applying these potentials for 60 seconds to the electrodes (3), through reduction from the solution, the metal ions are deposited as metals on the active electrode regions. In the following detection process each electrode, starting from the deposition potential is scanned 0.2 V to positive potential using the difference pulse polarography method. By scanning a potential window of 0.2 V positive in respect of the deposition potential applied to the respective electrode thus only one of the deposited metal ions is reoxidized and thus detected at one electrode. This procedure allows the detection of bismuth at the first electrode, copper at the second electrode, lead at the third electrode and cadmium at the fourth electrode or alternatively copper at the first electrode, lead at the second electrode, cadmium at the third electrode and zinc at the fourth electrode. This is a standard method, in which the oxidation flow can be very accurately determined for the particular metal on the corresponding electrode by stepped pulses and measurements at the start and finish of such a pulse. This oxidation flow is proportional to the metal concentration present in the solution. The concentration of the metals in the unknown solution is determined in that the measuring process is repeated with a solution of four metals of known concentrations and consequently the measurement is calibrated.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A process for electrochemical analysis of a solution, the process comprising the steps of:

bringing a silicon chip having arranged thereon a planar multi-electrode array including a reference electrode and several other electrodes into contact with the solution to be analyzed, said other electrodes each comprising an array of individual microstructured microelectrodes, with said reference electrode and each of said other electrodes being capable of independently receiving electrical steady-state and pulse potentials;

simultaneously depositing metal from the solution to be analyzed on said other electrodes such that each of said other electrodes formed of the array of individual microstructured microelectrodes is coated with one of a different metal and different metal mixture; and subsequently, approximately simultaneously oxidizing the deposited metals to metal ions on individual ones of said other electrodes formed of the array of individual microstructured microelectrodes to identify the metals;

wherein each of the individual microstructured microelectrodes has a surface area of 25 $\mu m^2$.

2. The process according to claim 1, wherein for the depositing of different metals, the method further comprises the step of simultaneously applying different potentials to the individual ones of the electrodes.

3. The process according to claim 2, wherein for approximately simultaneously identifying the metals deposited on the electrodes, the process further comprises the steps of approximately simultaneously scanning the individual ones of the electrodes formed of the arrayed individual microstructured microelectrodes in a different potential range through an application of one of a potential ramp and sequence of potential pulses; and selecting the potential ramp or sequence of potential pulses such that a different metal is identified on each electrode formed of the arrayed individual microstructured microelectrodes in a selective manner.

4. The process according to claim 1, wherein for approximately simultaneously identifying the metals deposited on the electrodes, the process further comprises the steps of approximately simultaneously scanning the individual ones of the electrodes formed of the arrayed individual microstructured microelectrodes in a different potential range through an application of one of a potential ramp and sequence of potential pulses; and selecting the potential ramp or sequence of potential pulses such that a different metal is identified on each electrode formed of the arrayed individual microstructured microelectrodes in a selective manner.

5. The process according to claim 1, wherein the electrodes are formed from one of a metal, metal oxide and carbon.

6. The process according to claim 1, wherein electrodes formed of platinum or gold are used during the process of electrochemical analysis.

7. The process according to claim 1, the process further comprising the step of:

coating at least one of the arrays of individual microstructured microelectrodes with a homogenous mercury film prior to analyzing the solution.

8. The process according to claim 7, wherein for said coating step, the method further comprising the step of bringing the at least one array of individual microstructured microelectrodes into contact with a mercury-containing electrolyte.

* * * * *